(12) United States Patent
Xie et al.

(10) Patent No.: US 12,215,394 B2
(45) Date of Patent: Feb. 4, 2025

(54) MOLECULAR MARKER NICOTINE ASSOCIATED SNP 1 FOR IDENTIFYING HIGH OR LOW NICOTINE CONTENT OF TOBACCO AND ITS KIT AS WELL AS USE THEREOF

(71) Applicant: Yunan Academy of Tobacco Agricultural Science, Kunming (CN)

(72) Inventors: He Xie, Kunming (CN); Ge Bai, Kunming (CN); Yong Li, Kunming (CN); Aiguo Yang, Kunming (CN); Tao Pang, Kunming (CN); Dahai Yang, Kunming (CN); Bingguang Xiao, Kunming (CN); Yongping Li, Kunming (CN); Min Ren, Kunming (CN); Mingliang Fei, Kunming (CN)

( * ) Notice: Subject to any disclaimer, the term of this patent is extended or adjusted under 35 U.S.C. 154(b) by 375 days.

(21) Appl. No.: 17/534,204

(22) Filed: Nov. 23, 2021

(65) Prior Publication Data
US 2023/0203601 A1    Jun. 29, 2023

(30) Foreign Application Priority Data
Nov. 10, 2021 (CN) .......................... 202111324714.4

(51) Int. Cl.
*C12Q 1/6895* (2018.01)
*A01H 1/04* (2006.01)
*G16B 20/20* (2019.01)

(52) U.S. Cl.
CPC ............ *C12Q 1/6895* (2013.01); *A01H 1/04* (2013.01); *G16B 20/20* (2019.02)

(58) Field of Classification Search
None
See application file for complete search history.

(56) References Cited

PUBLICATIONS

Fernandez-Pozo, Noe, et al. "The Sol Genomics Network (SGN)—from genotype to phenotype to breeding." Nucleic acids research 43.D1 (2015): D1036-D1041. (Year: 2015).*
GenBank Accession No. XM_009802118.1 "Predicted: Nicotiana sylvestris transcription factor MYC2-like (LOC104246317), mRNA" dated Oct. 21, 2014; https://www.ncbi.nlm.nih.gov/nucleotide/XM_009802118.1?report=genbank&log$=nucltop&blast_rank=1&RID=FNCS6CR3013 (Year: 2014).*

* cited by examiner

*Primary Examiner* — Charles Logsdon
*Assistant Examiner* — Kelsey L McWilliams
(74) *Attorney, Agent, or Firm* — Harness, Dickey & Pierce, P.L.C.; Anthony G. Fussner

(57) ABSTRACT

The present invention "A Molecular marker Nicotine Associated SNP 1 for identifying high or nicotine content of tobacco and its kit as well as use thereof" belongs to field of molecular biology technology. The molecular marker Nicotine Associated SNP 1 is a SNP Nitab4.5_0002539:95304 A/G at base No. 95304 of Genomic segment No. 0002539 in tobacco genome version of Nitab v4.5 Genome Scaffolds Edwards2017. The present invention can accurately identify and screen tobacco germplasm resources with high or low nicotine content, and the screened tobacco can be directly used for breeding new tobacco varieties without transgenic methods. At the same time, gene sequence where the SNP site is located can also significantly activate promoters of key enzyme genes in nicotine synthesis pathway.

6 Claims, 3 Drawing Sheets
Specification includes a Sequence Listing.

SEQUENCE LISTING

<160> NUMBER OF SEQ ID NOS: 13

<210> SEQ ID NO 1
<211> LENGTH: 36
<212> TYPE: DNA
<213> ORGANISM: Artificial Sequence
<220> FEATURE:
<223> OTHER INFORMATION: MYC2a-F1 primers

<400> SEQUENCE: 1
gtatcaagaa tcaaacagat ctgaattgat ttgtct                36

<210> SEQ ID NO 2
<211> LENGTH: 22
<212> TYPE: DNA
<213> ORGANISM: Artificial Sequence
<220> FEATURE:

<223> OTHER INFORMATION: MYC2a-R1 primers

<400> SEQUENCE: 2
tgataaagtc aggcgaaaac ga                                              22

<210> SEQ ID NO 3
<211> LENGTH: 40
<212> TYPE: DNA
<213> ORGANISM: Artificial Sequence
<220> FEATURE:
<223> OTHER INFORMATION: PMT2_Pgreen_0800_F

<400> SEQUENCE: 3
gtcgacggta tcgataagct tagtattcaa ggtatctaac                           40

<210> SEQ ID NO 4
<211> LENGTH: 40
<212> TYPE: DNA
<213> ORGANISM: Artificial Sequence
<220> FEATURE:
<223> OTHER INFORMATION: PMT2_Pgreen_0800_R primers

<400> SEQUENCE: 4
cgctctagaa ctagtggatc ctttcaaaat taaactaaac                           40

<210> SEQ ID NO 5
<211> LENGTH: 40
<212> TYPE: DNA
<213> ORGANISM: Artificial Sequence
<220> FEATURE:
<223> OTHER INFORMATION: QPT2_Pgreen_0800_F primers

<400> SEQUENCE: 5
gtcgacggta tcgataagct tgaaactata aatagctaag                           40

<210> SEQ ID NO 6
<211> LENGTH: 40
<212> TYPE: DNA
<213> ORGANISM: Artificial Sequence
<220> FEATURE:
<223> OTHER INFORMATION: QPT2_Pgreen_0800_R primers

<400> SEQUENCE: 6
cgctctagaa ctagtggatc cggtttattt tcttggggct                           40

<210> SEQ ID NO 7
<211> LENGTH: 54
<212> TYPE: DNA
<213> ORGANISM: Artificial Sequence
<220> FEATURE:
<223> OTHER INFORMATION: NtMYC2a_F primers

<400> SEQUENCE: 7
ggggacaagt ttgtacaaaa aagcaggctg catgacggat tatagaatac caac           54

<210> SEQ ID NO 8
<211> LENGTH: 56
<212> TYPE: DNA
<213> ORGANISM: Artificial Sequence
<220> FEATURE:
<223> OTHER INFORMATION: NtMYC2a_R primers

<400> SEQUENCE: 8
ggggaccact ttgtacaaga aagctgggtc tcatcgcgat tcagcaattc tggatg         56

```
<210> SEQ ID NO 9
<211> LENGTH: 33
<212> TYPE: DNA
<213> ORGANISM: Artificial Sequence
<220> FEATURE:
<223> OTHER INFORMATION: primers NtMED25 F

<400> SEQUENCE: 9
aaggtaccat gtgtaaaaat gcgttgggag ctg                    33

<210> SEQ ID NO 10
<211> LENGTH: 33
<212> TYPE: DNA
<213> ORGANISM: Artificial Sequence
<220> FEATURE:
<223> OTHER INFORMATION: primers NtMED25 R

<400> SEQUENCE: 10
aagtcgacgg gcatgtttgg cagtcctcgt gaa                    33

<210> SEQ ID NO 11
<211> LENGTH: 39
<212> TYPE: DNA
<213> ORGANISM: Artificial Sequence
<220> FEATURE:
<223> OTHER INFORMATION: primers NtMYC2 F

<400> SEQUENCE: 11
ttggtaccat gacggactat agaataccaa cgatgacta              39

<210> SEQ ID NO 12
<211> LENGTH: 39
<212> TYPE: DNA
<213> ORGANISM: Artificial Sequence
<220> FEATURE:
<223> OTHER INFORMATION: primers NtMYC2 R

<400> SEQUENCE: 12
aagtcgactc gcgattcagc aattctggat gtcaatgat              39

<210> SEQ ID NO 13
<211> LENGTH: 468
<212> TYPE: DNA
<213> ORGANISM: Artificial Sequence
<220> FEATURE:
<223> OTHER INFORMATION: amplicon sequence

<400> SEQUENCE: 13
gtatcaagaa tcaaacagat ctgaattgat ttgtctgttt tttttcttg atttttgttat      60 atggaatgac ggattataga ataccaacga tgactaatat atggagcaat actacatccg    120
atgataatat gatggaagct tttttatctt ctgatccgtc gtcgttttgg cccggaacaa    180
ctactacacc aactccccgg agttcagttt ctccagcgcc ggcgccggtg acggggattg    240
ccggagaccc attaaagtct atgccatatt tcaaccaaga gtcactgcaa cagcgactcc    300
agactttaat cgatggggct cgcgaagggt ggacgtatgc catattttgg caatcgtctg    360
ttgtggattt cgcgagcccc tcggttttgg ggtggggaga tgggtattat aaaggtgaag    420
aagataaaaa taagcgtaaa acggcgtcgt tttcgcctga ctttatca                 468
```

MOLECULAR MARKER NICOTINE ASSOCIATED SNP 1 FOR IDENTIFYING HIGH OR LOW NICOTINE CONTENT OF TOBACCO AND ITS KIT AS WELL AS USE THEREOF

SEQUENCE LISTING

This application contains references to amino acid sequences and/or nucleic acid sequences which have been submitted concurrently herewith as the sequence listing text file entitled "000027 us_SequenceListing.txt", file size 3,426 bytes, created on Jun. 25, 2024. The aforementioned sequence listing is hereby incorporated by reference in its entirety pursuant to 37 C.F.R. § 1.52 (e) (5).

TECHNICAL FIELD

The present invention relates to the field of molecular biology technology, in particular to a molecular marker Nicotine Associated SNP 1 for identifying high or low nicotine content of tobacco and its kit as well as application thereof.

BACKGROUND ART

It is a very meaningful work to study metabolic regulation of tobacco nicotine. Tobacco varieties with different nicotine content can be provided through genetic regulation, which can provide raw materials for tobacco commercial production of personalized nicotine tobacco products. Nicotine has a strong physiological stimulating effect on human body and is material basis for the commercial use of tobacco. Many of the world's top tobacco companies such as Philip Morris, Imperial Tobacco, Japan Tobacco, British American Tobacco and other companies have invested heavily in research on metabolic pathways and regulatory mechanisms of tobacco nicotine.

As the most important secondary metabolite of *Nicotiana tabacum*, and one of most well-known alkaloid, Nicotine is the most economically valuable part of tobacco whose content can directly determine quality of tobacco leaves. In most tobacco varieties, alkaloids account for 2%-4% of dry weight, while nicotine accounts for 90%-95% of total content of alkaloids.

When tobacco growth is invaded or stressed by insects and pathogenic bacteria, nicotine can be produced in tobacco plant by inducing to resist the invasion. Therefore, nicotine is a protective metabolite of tobacco itself, which provides protection for its normal growth and development. Too high or too low nicotine content in industrial production will lead to uncoordinated chemical content of tobacco leaves, reduce usability, and be unfavorable to cigarette production. Therefore, studying synthesis and metabolic regulation of tobacco nicotine is of great significance to development of our country's tobacco industry and agricultural production.

The biosynthetic pathway of nicotine has been partially resolved. Putrescine in tobacco can be used to synthesize nicotine pyrrolidine ring. Arginine decarboxylase (ADC) catalyzes decarboxylation of arginine to form putrescine, or ornithine decarboxylase (ODC) catalyzes decarboxylation of ornithine to form putrescine. Putrescine obtains methyl provided by S-adenosyl-L-methionine (SAM) under the action of putrescine-N-methyltransferase (PMT) to form N-methylputrescine, which is a reaction dependent on activity of S-adenosylmethionine synthase (SAMs). N-methylputrescine forms 4-methylamino butyl ether under catalysis of N-methylputrescine oxidase (MPO), and forms N-methyl-Δ1-pyrroline cation through self-ligation and then condenses with nicotinic acid derivatives providing pyridine ring to form nicotine.

The pyridine ring of nicotine is partially provided by nicotinic acid, and its precursor is quinolinic acid synthesized from aspartic acid. Quinolinic acid forms nicotinamide adenine dinucleotide (NAD) under the catalysis of quinolinate phosphoribosyl transferase (QPRT), and then generates nicotinic acid through pyridine nucleotide cycle pathway.

Recent studies on condensation reaction of nicotine pyrrolidine ring and pyridine ring showed that isoflavone reductase-like gene A622, a member of PIP family of NADPH dependent reductase, and its homologous genes are involved in this process. Plant hormone is one of the basic ways to regulate biosynthesis of secondary metabolites. Analyzing the regulatory mechanism of hormone signal on biosynthesis of secondary metabolites is one of the key points of plant science research. Jasmonates (JAs) have been proved to be widely involved in the metabolic regulation of plant secondary metabolites. JA has a significant inducing effect on nicotine biosynthesis.

In the presence of jasmonic acid, jasmonic acid derivative JA-Ile binds to jasmonic acid receptor COI1 to ubiquitin-mediated degrade the negative regulator JAZ protein, thereby releasing downstream transcriptional activators and activating the plant's jasmonic acid response. The jasmonic acid pathway regulators COI1 and JAZ protein of tobacco have been proved to be regulators of nicotine synthesis. Recent studies have also identified some transcription factors regulating nicotine synthesis, such as ERF transcription factor family members JAP1, ERF32 and ORC1 and their homologous genes, bHLH transcription factor family members bHLH1/2 and MYC2. These ERF transcription factors and bHLH transcription factors can also affect nicotine metabolism through mutual regulation.

At present, there is no molecular marker using SNP site to identify high or low nicotine content of tobacco in this field.

SUMMARY OF THE INVENTION

Based on the above-mentioned research gap in the field, purpose of the present invention is to provide a molecular marker Nicotine Associated SNP 1 for identifying high or low nicotine content of tobacco and its kit as well as use.

In order to achieve the above purpose, the technical solution of the present invention is as follows:

A molecular marker Nicotine Associated SNP 1 for identifying high or low nicotine content of tobacco, characterized in that, is a SNP site Nitab4.5_0002539:95304 A/G at base No. 95304 of Genomic segment No. 0002539 in tobacco genome version of Nitab v4.5 Genome Scaffolds Edwards2017.

A pair of specific primers for the molecular marker Nicotine Associated SNP 1 for identifying nicotine content of tobacco are shown as SEQ ID NO. 1 and SEQ ID NO. 2.

A kit for identifying high or low nicotine content of tobacco, characterized in that, comprises a molecular marker Nicotine Associated SNP 1, the molecular marker Nicotine Associated SNP 1 is a SNP site Nitab4.5_0002539:95304 A/G at base No. 95304 of Genomic segment No. 0002539 in tobacco genome version of Nitab v4.5 Genome Scaffolds Edwards2017.

The kit for identifying high or low nicotine content of tobacco also comprises: a pair of specific primers for the molecular marker Nicotine Associated SNP 1;

Preferably, the specific primers for the molecular marker Nicotine Associated SNP 1 are shown as SEQ ID NO. 1 and SEQ ID NO. 2;

Preferably, the kit also comprises: reagents for PCR, reagents for sequencing, and/or reagents for KASP (Kompetitive Allele Specific PCR) genotyping assay;

Preferably, the reagents for PCR comprise: dNTPs, Taq enzyme, PCR buffer, ddH2O;

Preferably, the reagents for sequencing comprise: Tris-HCl, agarose, EB;

Preferably, the reagents for KASP (Kompetitive Allele Specific PCR) genotyping assay comprise: KASP® Master mix.

A method for identifying high or low nicotine content of tobacco, characterized in that, a molecular marker Nicotine Associated SNP 1 is used to screen candidate tobaccos; the molecular marker Nicotine Associated SNP 1 is a SNP site Nitab4.5_0002539:95304 A/G at base No. 95304 of Genomic segment No. 0002539 in tobacco genome version of Nitab v4.5 Genome Scaffolds Edwards2017.

The method for identifying high or low nicotine content of tobacco comprises: a pair of specific primers for the molecular marker Nicotine Associated SNP 1 are used for PCR amplification on DNA of candidate tobaccos; the specific primers for the molecular marker Nicotine Associated SNP 1 are shown as SEQ ID NO. 1 and SEQ ID NO. 2;

Preferably, the method for identifying high or level nicotine content of tobacco also comprises: PCR products are subjected to sequencing or KASP (Kompetitive Allele Specific PCR) genotyping assayassay;

Preferably, results of sequencing or KASP (Kompetitive Allele Specific PCR) genotyping assayassay show that the candidate tobaccos whose SNP site genotype is GG is a tobacco with low nicotine content;

Preferably, results of sequencing or KASP (Kompetitive Allele Specific PCR) genotyping assay show that the candidate tobaccos whose SNP site genotype is AA is a tobacco with high nicotine content;

Preferably, the PCR reaction system comprises:
Template 0.02 µL/µL, forward primer 0.02 µL/µL, reverse primer 0.02 µL/µL, 5×buffer 0.2 µL/µL, dNTP mixture 0.02 µL/µL, DNA polymerase 0.02 µL/µL, the rest is water;
The PCR amplification reaction program includes: 98° C. 5 min; taking 98° C. 30 s, 58° C. 30 s, 72° C. 30 s as 1 cycle, a total of 35 cycles; 72° C. 5 min;

Preferably, DNA of the candidate tobacco is extracted from tobacco leaves, seeds, roots, stems, flowers, or fruits.

A method for breeding tobacco varieties with high or low nicotine content, characterized in that, tobaccos with high or low nicotine content from candidate tobaccos are screened by using the molecular marker Nicotine Associated SNP 1 for identifying high or low nicotine content of tobacco, and/or the kit for identifying high or low nicotine content of tobacco, and/or the method for identifying high or low nicotine content of tobacco.

Tobacco with high nicotine content is selected as female parent or male parent, and tobacco required to be improved is taken as male parent or female parent, F1 generation is obtained by crossing the female parent and the male parent.

Preferably, F2 generation plants are obtained by inbred F1 generation plants, and F2 generation plants are backcrossed with selected tobaccos with high or low nicotine content or tobaccos required to be improved;

Tobaccos with high or low nicotine content are screened from the backcrossed population through the method for identifying high or low nicotine content of tobacco, and/or the molecular marker Nicotine Associated SNP 1 for identifying high or low nicotine content of tobacco, and/or the kit for identifying high or low nicotine content of tobacco.

A method for activating promoters of genes involving nicotine synthesis pathway of tobacco, characterized in that, overexpressing genes containing SNP site; the SNP site are a SNP site of a molecular marker Nicotine Associated SNP 1 for identifying high or low nicotine content of tobacco; the molecular marker Nicotine Associated SNP 1 is SNP site Nitab4.5_0002539:95304 A/G at base No. 95304 of Genomic segment No. 0002539 in tobacco genome version of Nitab v4.5 Genome Scaffolds Edwards2017.

Preferably, primers shown as SEQ ID NO. 7 and SEQ ID NO. 8 are used to amplify DNA of tobaccos with high or low nicotine content to obtain gene sequence containing the SNP site;

Preferably, primers shown as SEQ ID NO. 3 and SEQ ID NO. 4, or SEQ ID NO. 5 and SEQ ID NO. 6 are used to amplify DNA of tobaccos to obtain promoter sequence of genes involving tobacco nicotine synthesis pathway;

Preferably, gene sequence containing the SNP site is connect into overexpression vector, and sequence of gene involving nicotine synthesis pathway of tobacco is connected into expression vector;

Preferably, the overexpression vector connecting the gene sequence containing the SNP site and the expression vector connecting the sequence of gene involving nicotine synthesis pathway of tobacco are transformed into *agrobacterium* and then transfected into tobacco;

Preferably, the promoters of genes involving nicotine synthesis pathway are selected from promoters of the following genes: NtPMT2 and/or NtQPT2; Preferably, the overexpression vector is pB2GW7 overexpression vector; the expression vector is pGreen0800 fluorescent expression vector.

A method for strengthening interaction to gene promoting nicotine synthesis, characterized in that, the genes promoting nicotine synthesis and gene fragments containing SNP site are co-expressed; The SNP site is a SNP site of a molecular marker nicotine associated SNP 1 for identifying high or low nicotine content of tobacco; the molecular marker Nicotine Associated SNP 1 is a SNP site Nitab4.5_0002539:95304 A/G at base No. 95304 of Genomic segment No. 0002539 in tobacco genome version of the Nitab v4.5 Genome Scaffolds Edwards2017.

Preferably, primers shown as SEQ ID NO. 9 and SEQ ID NO. 10 are used to amplify sequence of the gene promoting nicotine synthesis;

Preferably, the primers shown as SEQ ID NO. 11 and SEQ ID NO. 12 are used to amplify the gene fragment containing SNP site;

Preferably, the sequence of the gene promoting nicotine synthesis and the gene fragment containing SNP site are respectively connected into expression vector to perform the co-expression;

Preferably, the expression vector connected with the sequence of the gene promoting nicotine synthesis and the expression vector connected with the gene fragment containing SNP site are co-transformed tobacco;

Preferably, the gene promoting nicotine synthesis is NtMED25, and the expression vector is pCAMBIA1300-cLUC or pCAMBIA 1300-nLUC.

The present invention provides a SNP (Single Nucleotide Polymorphism) site Nicotine Associated SNP 1 associated with tobacco nicotine content traits, characterized in that: the SNP site is a SNP Nitab4.5_0002539:95304 A/G at base No.

95304 of Genomic segment No. 0002539 in tobacco genome version of Nitab v4.5 Genome Scaffolds Edwards2017.

The SNP (Single Nucleotide Polymorphism) site associated with tobacco nicotine content traits.

The method for GWAS analysis of SNP (single nucleotide polymorphism) site associated with tobacco nicotine content traits, characterized in that, comprises the following steps: 1) Senteion software is used to detect SNPs of tobacco population, and a total of 47140188 SNP sites are obtained by said detection. 2) SNPs are filtered through vcftools software with conditions of Miss0.5, Het0.2, and maf0.05, and finally a total of 6,957,682 high-quality SNP sites are obtained for subsequent analysis. 3) SVs analysis is performed on multiple natural tobacco populations by using BreakDancer and CNVnator standards Analysis process; 4) Based on analysis of population structure and genetic relationship, whole genome association analysis is performed on the phenotypic data of tobacco nicotine content by using the mixed linear model method.

Use of the SNP (single nucleotide polymorphism) site associated with tobacco nicotine content in early predicting and screening of tobacco nicotine content level.

Use of the SNP (single nucleotide polymorphism) site associated with tobacco nicotine content traits in tobacco molecular marker assisted breeding.

The SNP (single nucleotide polymorphism) site associated with tobacco nicotine content traits is used in tobacco breeding with high or low nicotine content.

A SNP (single nucleotide polymorphism) site associated with tobacco nicotine content traits, the SNP site is a SNP Nitab4.5_0002539:95304 A/G at base No. 95304 of Genomic segment No. 0002539 in tobacco genome version of Nitab v4.5 Genome Scaffolds Edwards2017.

Use of the SNP (Single Nucleotide Polymorphism) site associated with tobacco nicotine content in early predicting and screening tobacco nicotine content level.

Use of a SNP (Single Nucleotide Polymorphism) site associated with tobacco nicotine content traits in tobacco molecular marker assisted breeding.

A SNP (Single Nucleotide Polymorphism) site associated with tobacco nicotine content traits is used in tobacco breeding with high or low nicotine content.

The present invention has advantages as follows: the present invention identifies SNP (single nucleotide polymorphism) site associated with tobacco nicotine content traits, clarifies a new function of NtMYC2a and provides methods for its use, which lays a foundation for breeding tobacco with different nicotine content. GWAS analysis based on SNPs is used to identify SNP (single nucleotide polymorphism) site and genes that control tobacco nicotine content traits, and lay a foundation for molecular marker-assisted breeding and pyramiding breeding to change tabacco nicotine content.

The present invention provides a SNP (Single Nucleotide Polymorphism) site associated with tobacco nicotine content and a GWAS analysis method and its use. The SNP site is a SNP site with a base change of A/G which located at base No. 95304 of Genomic segment No. 0002539 in tobacco genome version of Nitab v4.5 Genome Scaffolds Edwards2017.

This site is an A/G SNP at base No. 95304 in Genomic segment No. 0002539 of tobacco genome version of Nitab v4.5 Genome Scaffolds Edwards 2017. The present invention uses SNP-based GWAS analysis to identify that the key site controlling tobacco nicotine content is the SNP site Nitab4.5_0002539:95304 A/G at base No. 95304 of Genomic segment No. 0002539 in tobacco genome version of Nitab v4.5 Genome Scaffolds Edwards2017.

Identification of this SNP helps to understand the biological function of NtMYC2a, and at the same time lays a foundation for molecular marker-assisted breeding and Pyramiding breeding to change tobacco nicotine content.

The present invention uses the Genome wide association study (GWAS) method to identify SNP site that have a major effect on tobacco nicotine content from 339 tobacco materials. Therefore, tobacco varieties with high nicotine content or low nicotine content can be bred based on assistance of said SNP site by the conventional method of crossing and then backcrossing. It can be used to provide gene resources for breeding tobacco with different nicotine contents, but also to provide marker information for molecular marker assisted breeding of tobacco, accelerating progress in breeding of tobacco with different nicotine contents. Under assistance of said SNP site, the present invention is available to directly enter tobacco breeding link without transgenic methods.

EMBODIMENTS

Figure 1:
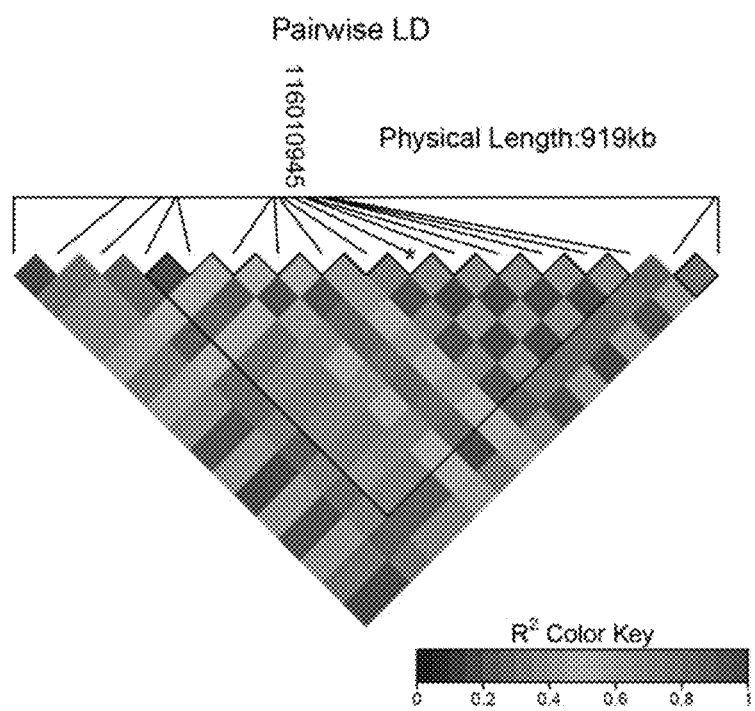
FIG. 1 is a LD heatmap of SNP on Chr8 chromosome of experimental example 1 of the present invention.

The present invention will be further illustrated with the following specific examples, but the protection scope is not limited by these examples.

Source of Biological Material 339 tobacco materials used in experimental example 1 and the 17 tobacco materials used in experimental example 2 of the present invention are all tobacco germplasm resources owned by the applicant. The applicant promises to distribute to the public within 20 years from the filing date of the present invention for verifying effect of the present invention.

Honghua Daijinyuan tobacco used in experimental examples 3 and 4 and Yunyan 87 tobacco used in experimental examples 3 and 4 are well-known tobacco varieties, which are commercially available. Ben's tobacco plants used in experiment example 3 are common experimental tobacco resources all over the world, which can be purchased commercially.

Agrobacterium used in experiment 3 is commercially available.

The 1$^{st}$ Group of Examples: The Molecular Marker of the Invention

This group of examples provides a molecular marker nicotine associated SNP 1 (nicas1) for identifying high or low nicotine content of tobacco. All embodiments in this group have the following common features: said molecular marker nicas1 for identifying high or low nicotine content of tobacco of this invention is a SNP Nitab4.5_0002539:95304 A/G at base No. 95304 of Genomic Segment No. 0002539 in tobacco genome version of Nitab v4.5 Genome Scaffolds Edwards2017; the SNP site is located at the 324th nucleotide of the amplicon sequence set forth in SEQ ID NO: 13, which is derived from the tobacco genome using primers set forth in SEQ ID NO: 1 and SEQ ID NO:2. The nucleotide of the SNP site is G or A. It is verified that the nucleotide of said SNP site of tobacco with high nicotine content is A, and the nucleotide of said SNP site of tobacco with low nicotine content is G. Furthermore, The molecular marker nicas1 can be used to accurately screen tobacco varieties with high nicotine content or low nicotine content and confirm their genotype and phenotype. Tobacco genome version of the invention is Nitab v4.5 Genome Scaffolds Edwards2017.

Amplicon sequence comprising the molecular marker nicas1:

```
                                         (SEQ ID NO: 13)
GTATCAAGAATCAAACAGATCTGAATTGATTTGTCTGTTTTTTTTCTT

GATTTTGTTATATGGAATGACGGATTATAGAATACCAACGATGACTAAT

ATATGGAGCAATACTACATCCGATGATAATATGATGGAAGCTTTTTAT

CTTCTGATCCGTCGTCGTTTTGGCCCGGAACAACTACTACACCAACTCC

CCGGAGTTCAGTTTCTCCAGCGCCGGCGCCGGTGACGGGGATTGCCGGA

GACCCATTAAAGTCTATGCCATATTTCAACCAAGAGTCACTGCAACAGC

GACTCCAGACTTTAATCGATGGGCTCGCGAAGGGTGGACGTATGCCAT

ATTTTGGCAATCGTCTGTTGTGGATTTCGCGAGCCCCTCGGTTTTGGGG

TGGGGAGATGGGTATTATAAAGGTGAAGAAGATAAAAATAAGCGTAAAA

CGGCGTCGTTTTCGCCTGACTTTATCA.
```

In specific embodiments, sequences of primers for amplifying the molecular marker nicas1 for identifying high or low nicotine content of tobacco are as shown in SEQ ID No. 1 and SEQ ID NO. 2:

```
MYC2a-F1
                                         (SEQ ID NO. 1)
GTATCAAGAATCAAACAGATCTGAATTGATTTGTCT,

MYC2a-R1
                                         (SEQ ID NO. 2)
TGATAAAGTCAGGCGAAAACGA .
```

Said SNP genotype can be distinguished by using above primers through detecting amplification products by KASP (Kompetitive Allele Specific PCR) labeling method, and person skilled in the art can also use other detection methods, such as caps labeling method, etc. He can design other available primers suitable for different detection methods according to said SNP site.

The 2$^{nd}$ Group of Examples: A Kit for Identifying the Nicotine Content of Tobacco of this Invention This group of examples provides a kit for identifying high or low nicotine content of tobacco. All embodiments in this group have the following common features: The kit comprises: said molecular marker nicas1; the molecular marker nicas1 is a SNP Nitab4.5_0002539:95304 A/G at base No. 95304 of Genomic segment No. 0002539 in tobacco genome version of Nitab v4.5 Genome Scaffolds Edwards2017; the SNP site is located at the 324th nucleotide of the amplicon sequence set forth in SEQ ID NO: 13, which is derived from the tobacco genome using primers set forth in SEQ ID NO: 1 and SEQ ID NO:2.

Preferably, the kit also comprises: a pair of specific primers for the molecular marker Nicotine Associated SNP 1; preferably, the specific primers for the molecular marker Nicotine Associated SNP 1 are shown as SEQ ID NO. 1 and SEQ ID NO. 2;

Preferably, the kit also comprises: reagents for PCR, reagents for sequencing, and/or reagents for KASP (Kompetitive Allele Specific PCR) genotyping assay;

Preferably, the reagents for PCR comprise: dNTPs, Taq enzyme, PCR buffer, ddH2O;

Preferably, the reagents for sequencing comprise: Tris-HCl, agarose, EB;

Preferably, the reagents for KASP (Kompetitive Allele Specific PCR) genotyping assay comprise: KASP® Master mix.

The 3$^{rd}$ Group of Examples: A Method for Identifying High or Low Nicotine Content of Tobacco of this Invention This group of examples provides a method for identifying high or low nicotine content of tobacco. All embodiments in this group have the following common features: candidate tobaccos are screened by said molecular marker nicas1; the molecular marker nicas1 is a SNP Nitab4.5_0002539:95304 A/G at base No. 95304 of Genomic segment No. 0002539 in tobacco genome version of Nitab v4.5 Genome Scaffolds Edwards2017; the SNP site is located at the 324th nucleotide of the amplicon sequence set forth in SEQ ID NO:13, which is derived from the tobacco genome using primers set forth in SEQ ID NO: 1 and SEQ ID NO:2.

In specific embodiments, the method for identifying high or low nicotine content of tobacco comprises: a pair of specific primers for the molecular marker Nicotine Associated SNP 1 are used for PCR amplification on DNA of the tobacco material to be tested; the specific primers for the molecular marker Nicotine Associated SNP 1 are shown as SEQ ID NO. 1 and SEQ ID NO. 2;

Preferably, the method for identifying high or low nicotine content of tobacco also comprises: PCR amplification products are subjected to sequencing or KASP (Kompetitive Allele Specific PCR) genotyping assay;

Preferably, result of sequencing or KASP (Kompetitive Allele Specific PCR) genotyping assay shows that candidate tobacco whose SNP site genotype is GG is a tobacco with low nicotine content;

result of sequencing or KASP (Kompetitive Allele Specific PCR) genotyping assay shows that candidate tobacco whose SNP site genotype is AA is a tobacco material with high nicotine content;

Preferably, reaction system and reaction procedure for PCR amplification are shown in Table 1 below:

TABLE 1

| PCR system: 50 μL system | |
| --- | --- |
| Template DNA | 1 μL |
| primer-F (10 μmol/L) | 1 μL |
| primer-R (10 μmol/L) | 1 μL |
| 5× buffer | 10 μL |
| dNTP mixture (10 mmol/L) | 1 μL |
| Phusion DNA Polymerase | 0.5 μL |
| ddH$_2$O | Up to 50 μL |
| PCR procedure | |
| ① 98° C. | 5 min |
| ② 98° C. | 30 s |
| ③ 58° C. | 30 s |
| ④ 72° C. | 30 s |
| ②-④ | 35 cycles |
| ⑤ 72° C. | 5 min |
| 4° C. | Forever |

Preferably, DNA of candidate tobacco is extracted from tobacco leaves, seeds, roots, stems, flowers, or fruits.

KASP (Kompetitive Allele Specific PCR) is a well-known technology in the art. Person skilled in the art can make routine selection and adjustment according to the specific conditions of experiment practice with reference to the conventional technical means in the art. For example, "KASP® Master mix" can be purchased and its reaction conditions can follow record of its product manual. According to fragment size of PCR amplification products obtained by the invention, suitable parameters and reaction conditions are selected and adjusted.

KASP (Kompetitive Allele Specific PCR) and DNA sequencing are both well-known technologies in the art and also mature commercialized technologies in the market at present. Person skilled in the art can perform PCR amplification according to the primer sequences disclosed in the invention, send the amplification product to company that is professional for KASP (Kompetitive Allele Specific PCR) and DNA sequencing for detecting PCR amplification product, so as to obtain the fragment size or specific sequence of the PCR amplification product. Whether phenotype of candidate tobacco is high nicotine content type or low nicotine content type is determined according to PCR products amplified based on DNA template of candidate tobacco show whether genotype of the SNP site is AA or GG.

Person skilled in the art can also use other conventional methods in the art to detect PCR amplification products. For example, competitive allele-specific PCR amplification, electrophoresis, DNA sequencing and other methods can be used to obtain the PCR amplification product sequence, and then learn whether phenotype of candidate tobacco is low nicotine content type tobacco or high nicotine content type tobacco.

In other embodiments, Kluster Caller genotyping instrument can be used to detect the sequence of PCR products.

The Kluster Caller genotyping instrument is a common instrument in this field that can be purchased commercially, and its operation can be performed according to the product manual of the instrument.

The 4$^{th}$ Group of Examples: A Method for Selecting Tobacco Varieties with High or Low Nicotine Content of the Invention This group of examples provides a method for selecting tobacco varieties with high or low nicotine content. All embodiments in this group have the following common features: the method for identifying high or low nicotine content in tobacco provided by any of the 3$^{rd}$ group of examples is used to screen tobacco with high or low nicotine content from candidate tobaccos.

Person skilled in the art can screen tobaccos at any growth stage of tobacco plants by the method of identifying high or low nicotine content of tobacco, and obtain tobaccos with high or low nicotine content.

In further embodiments, F1 generation is obtained by crossing the selected tobacco with high or low nicotine content as female parent or male parent and tobacco required to be improved as male parent or female parent.

Preferably, F2 generation plants are obtained by inbred F1 generation plants, and F2 generation plants are backcrossed with selected tobaccos with high or low nicotine content or tobaccos required to be improved;

preferably, tobaccos with high or low nicotine content are screened from the backcrossed population through the method for identifying high or low nicotine content of tobacco according to any of the 3$^{rd}$ group of examples, and/or the molecular marker Nicotine Associated SNP 1 for identifying high or low nicotine content of tobacco according to any of the 1$^{st}$ group of examples, and/or the kit for identifying high or low nicotine content of tobacco according to any of the 2$^{nd}$ group of examples.

The 5$^{th}$ Group Examples: A Method for Activating Gene Promoters of Genes Involving Tobacco Nicotine Synthesis Pathway of this Invention This group of examples provides a method for activating promoters of gene involving tobacco nicotine synthesis pathway. All embodiments in this group have the following common features: overexpressing genes containing SNP site; the SNP site are the SNP site of a molecular marker Nicotine Associated SNP 1 for identifying high or low nicotine content of tobacco; the molecular marker Nicotine Associated SNP 1 is a SNP Nitab4.5_0002539:95304 A/G at base No. 95304 of Genomic segment No. 0002539 in tobacco genome version of Nitab v4.5 Genome Scaffolds Edwards2017; the SNP site is located at the 324$^{th}$ nucleotide of the amplicon sequence set forth in SEQ ID NO:13, which is derived from the tobacco genome using primers set forth in SEQ ID NO: 1 and SEQ ID NO:2.

In some embodiments, the base of the SNP site in the gene containing the SNP site is A or G;

In specific embodiments, primers shown as SEQ ID NO. 7 and SEQ ID NO. 8 are used to amplify DNA of tobacco with high nicotine content or low nicotine content to obtain the gene sequence containing the SNP site;

In preferable embodiments, primers shown as SEQ ID NO. 3 and SEQ ID NO. 4, or SEQ ID NO. 5 and SEQ ID NO. 6 are used to amplify DNA of tobacco to obtain sequences of genes involving tobacco nicotine synthesis pathway;

In other embodiments, sequence of gene containing the SNP site is connected into a overexpression vector, and sequence of genes involving tobacco nicotine synthesis pathway is connected into a expression vector;

In further embodiments, the overexpression vector connected with sequence of gene containing the SNP site and the expression vector connected with sequence of gene involving tobacco nicotine synthesis pathway are transformed into *agrobacterium* and then transfected tobacco;

In specific embodiments, the promoters of genes involving nicotine synthesis pathway are selected from promoters of the following genes: NtPMT2 and/or NtQPT2;

In further embodiments, the overexpression vector is a pB2GW7 overexpression vector; the expression vector is a pGreen0800 fluorescent expression vector.

The 6$^{th}$ group of examples: a method for enhancing gene interaction of this invention This group of examples provides a method for enhancing interaction between genes promoting nicotine synthesis. All embodiments in this group have the following common features: genes promoting nicotine synthesis are co-expressed with gene fragments containing SNP site; The SNP site is the SNP site of a molecular marker nicotine associated SNP 1 for identifying high or low nicotine contents of tobacco. The molecular marker Nicotine Associated SNP 1 is a SNP Nitab4.5_0002539:95304 A/G at base No. 95304 of Genomic segment No. 0002539 in tobacco genome version of Nitab v4.5 Genome Scaffolds Edwards2017.

In some embodiments, base of the SNP site in the gene containing the SNP site is A or G;

Preferably, the primers shown as SEQ ID NO. 9 and SEQ ID NO. 10 are used to amplify nicotine synthesis-promoting gene sequence;

Preferably, the primers shown as SEQ ID NO. 11 and SEQ ID NO. 12 are used to amplify the gene fragment containing the SNP site;

Preferably, the amplified nicotine synthesis-promoting gene sequence and the gene fragment containing the SNP site are respectively connected into an expression vector to perform the co-expression;

Preferably, an expression vector connected with the nicotine synthesis-promoting gene sequence and an expression vector connected with the gene fragment containing the SNP site are co-transformed into tobacco;

Preferably, the nicotine synthesis-promoting gene or the gene promoting nicotine synthesis is NtMED25, and the expression vector is pCAMBIA1300-cLUC or pCAMBIA 1300-nLUC.

Compared with AA genotype of the SNP site, GG genotype of the SNP site can significantly improve interaction effect with NtMED25 gene.

Experimental Example 1: Obtaining the Molecular Marker of the Present Invention

A SNP (Single Nucleotide Polymorphism) site associated with tobacco nicotine content traits, position of the SNP site is a SNP Nitab4.5_0002539:95304 A/G at base No. 95304 of Genomic segment No. 0002539 in tobacco genome version of Nitab v4.5 Genome Scaffolds Edwards2017. The SNP site is located at base No. 259 in coding region of gene NtMYC2a.

A method for GWAS analysis of SNP (single nucleotide polymorphism) site associated with tobacco nicotine content traits, comprising the following steps:
1. Senteion software is used for detecting population SNPs, and a total of 47140188 SNP sites have been obtained;
2. SNPs is filtered through vcftools software with conditions of Miss0.5, Het0.2, and maf0.05, and finally a total of 6,957,682 high-quality SNP site are obtained for subsequent analysis;
3. BreakDancer and CNVnator standard analysis procedures are used to perform SVs analysis on multiple natural tobacco populations;
4. Based on analysis of population structure and genetic relationship, the mixed linear model method is used to perform genome wide association study on phenotypic data of tobacco nicotine content traits. When performing genome-wide association study, significance thresholds of association between all tested traits and SNP sites are evaluated using the following formula, P=0.05/n, where n is the number of detected SNPs.

The present invention uses SNP to classify the phenotypic traits of 339 GWAS tobacco seeds and finds that there are 53 tobaccos with "GG" genotype and 286 tobaccos with "AA" genotype among 339 GWAS tobacco seeds.

The present invention conducted a detailed analysis on GWAS interval about 900 kb in tobacco genome, found that this area contains a total of 12 genes (\*, \*\*, \*\*) and 2 obvious LD blocks (Table 2, FIG. 1), and discovered a strong signal SNP associated with nicotine content traits (−logP=11.41, Nitab4.5_0002539:95304 A/G.), which is located as a SNP Nitab4.5_0002539:95304 A/G at base No. 95304 of Genomic segment No. 0002539 in tobacco genome version of Nitab v4.5 Genome Scaffolds Edwards2017, which is also located in an exon of MYC2a transcription factor protein (CASP) gene (Ga08G0117). It is an A-G SNP variation, and the corresponding amino acid variation is Glutamic acid-Lysin, indicating that this SNP variation of NtMYC2a may be a key variation that determines nicotine content.

Experimental Example 2: SNP Molecular Marker the Present Invention Identifying Tobaccos with High or Low Nicotine Content Determination of Nicotine Content in Tobacco Leaves Nicotine content of tobaccos was detected according to the standard YC/T 160-2002. The selected tobacco materials were non-transgenic tobacco plants and transgenic tobacco plants with similar developmental phenotypes which were all in vigorous growing stage, and wild-type tobacco K326 was used as the control. The upper, middle and lower leaves of 5 non-transgenic tobacco plants and transgenic tobacco plants were taken as one group. For the another group, 5 non-transgenic tobacco plants and transgenic tobacco plants were topped, and then the upper, middle and lower leaves of non-transgenic tobacco plants and transgenic tobacco plants were taken.

Tobacco samples were extracted with 5% acetic acid aqueous solution. The total alkaloids (calculated as nicotine) in the extract reacted with p-amino benzene sulfonic acid and cyanogen chloride, which was produced by the on-line reaction of potassium cyanide and chloramine T. The reaction products were measured at 460 nm with a colorimeter.

Main instruments and equipment: continuous flow analyzer (American API) (German SEAL AA3) (French ALLIANCE).

Reagent Preparation:

Buffer solution A: 2.35 g sodium chloride (NaCl) and 7.60 g sodium borate ($Na_{2a4}O_3 \cdot 10H_2O$) were weighed dissolved with water, transferred into a 1 L volumetric flask, and then 1 ml Brij 35 was added diluted to 1 L with distilled water, filtered with qualitative filter paper before use.

Buffer solution B: 26 g disodium hydrogen phosphate ($Na_2HPO_4$), 10.4 g citric acid [$COH(COOH)(CH_2COOH)_2 \cdot H_2O$], 7 g p-amino benzene sulfonic acid ($NH_2C_6H_4SO_3H$) were weighed and dissolve with water, transfer into a 1 L volumetric flask, and then 1 ml Brij 35 was added diluted to 1 L with distilled water, filtered with qualitative filter paper before use.

Chloramine T solution (N-chloro-4-methylphenylthioamide sodium salt) [$CH_3C_6H_4SO_2N$ (Na) $Cl \cdot 3H_2O$]: 8.65 g of chloramine T was dissolved in water, transferred into 500 ml volumetric flask, fixed volume by adding water, and filtered with qualitative filter paper before use.

0.22 mol/L NaOH buffer: NaOH 8.8 g, $Na_2HPO_4$ 26.0 g, $C_6H_8O_7 \cdot H_2O$ (citric acid monohydrate) were dissolved with water to 1000 ml.

P-aminobenzene sulfonic acid buffer: $C_6H_7NO_3S$ (p-amino benzene sulfonic acid) 7 g, $Na_2HPO_4$ 26.0 g and $C_6H_8O_7 \cdot H_2O$ (citric acid monohydrate) 10.4 g were dissolved with water to 1000 ml.

Chloramine T: chloramine T 1.2 g was dissolve with pure water to 100 ml, and stored in a brown reagent bottle.

Potassium cyanide: KCN 0.4 g was dissolved with pure water to 100 ml.

$NaCO_3$ solution: 10 g NaCO3 was dissolved in distilled water to 1000 ml.

Analysis steps: 0.3 g tobacco was placed into 150 ml triangular bottle or plastic bottle (accurate to 0.0001 g), 50 ml of 5% acetic acid solution was added into triangular bottle or plastic bottle with stopper covered; said triangular bottle or plastic bottle was shaken and extracted on an ordinary shaking table for 30 min, with the rotating speed controlling at 170 R/min. The extract was filtered with filter paper and detected by instrument. (Dilution is required if concentration of sample solution exceeds concentration range of the working standard solution).

Calculation and Expression of Results:

The content of total alkaloids on a dry basis is obtained from the following formula:

$$\text{total alkaloids (\%)} = \frac{C \times V}{m \times (1 - W)} \times 100$$

Wherein:

C—observation value of total alkaloids in sample solution, unit: mg/ml;
V—volume of extract, unit: ml;
M—mass of the sample, unit: Mg;
W—moisture content of the sample, unit: %.

The average value of two detected values is taken as the determination result, and the result is accurate to 0.01%.

In this disclosure, tobaccos with nicotine content >20 mg/g are tobaccos with high nicotine content whose genotype is AA;

Tobaccos with nicotine content ≤20 mg/g are tobaccos with low nicotine content whose genotype is GG.

Additional 17 candidate tobacco were verified by using the molecular marker of the invention, and the identification results are shown in Table 2 below:

TABLE 2

| SNP genotype | tobacco variety | nicotine content (mg/g) |
|---|---|---|
| AA | TI 516 | 31 |
| AA | TI 401 | 27 |
| AA | TI 383 | 21.5 |
| AA | TI 1457 | 27.5 |
| AA | TN90 | 24 |
| AA | Burley 21 | 22.5 |
| AA | TI 319 | 22.5 |
| AA | TI 179 | 21.1 |
| AA | HondDa | 21.4 |
| GG | TI 245 | 17.5 |
| GG | TW 7 | 2.5 |
| GG | TI 857 | 13.5 |
| GG | SC 72 | 13 |
| GG | K 399 | 18.5 |
| GG | YanYan97 | 10.25 |
| GG | YunYan87 | 9.4 |
| GG | YunYan02 | 9.1 |

Through detection of the molecular marker nicas1 and the identification method of the invention, among 17 candidate tobaccos, all of 17 tobaccos are consistent with the genotype and phenotype, wherein 9 tobaccos are of AA genotype and 8 tobaccos are of GG genotype. The SNP marker and the method of the invention identify tobaccos with high or low nicotine content with accuracy as high as 100%.

Experimental Example 3: Overexpression of SNP Site Gene Activates Nicotine Synthesis Related Enzyme Gene Promoter Promoter fragment of tobacco NtPMT2 gene was cloned with PMT2_Pgreen_0800_F primer gtcgacggtatcgataagctt-AGTATTCAAGGTATCTAAC (SEQ ID NO. 3) and PMT2_Pgreen_0800_R primer cgctctagaactagtggatccTTT-CAAAATTAAACTAAAC (SEQ ID NO. 4), and then the fragment was cloned into pGreen0800 fluorescent vector. Promoter sequence of NtQPT2 gene was cloned with QPT2_Pgreen_0800_F primer gtcgacggtatcgataagctt-GAAACTATAAATAGCTAAG (SEQ ID NO. 5) and QPT2_Pgreen_0800_R primer cgctctagaactagtg-gatccGGTTTATTTTCTTGGGGCT (SEQ ID NO. 6), and then cloned into pGreen0800 vector again. The cDNA of Honghua Daijinyuan and Yunyan 87 were amplified respectively with NtMYC2a F primer GGGGACAAGTTTGTA-CAAAAAAGCAGGCTGCATGACGGATTATAGAA-TACC AAC (SEQ ID NO. 7 and NtMYC2a R primer GGGGACCACTTTGTACAAGAAAGCTGGGTCT-CATCGCGATTCAGCAATTCT GGATG (SEQ ID NO. 8), and gene sequences of NtMYC2a of different genotypes were obtained, in which genotype of SNP site of Honghua Daijinyuan was A and genotype of SNP site of Yunyan 87 was G. Two fragments were cloned into PDONR-Zeo vector by BP reaction of geteway. Sequence fragment was finally introduced into pb2gw7 overexpression vector by LR reaction. After that, was adopted to these vectors were transformed into *agrobacterium* the chemical transformation method. *Agrobacterium* mono clones were picked and cultured in 2 ml of resistance liquid medium overnight, and 2 ml of broth was put into 50 ml resistance medium for cultivation the next day, and *agrobacterium* sediments were collected until OD value reached 0.6.

*Agrobacterium* injection is prepared according to the following combination in Table 3:

TABLE 3

Figure 2:
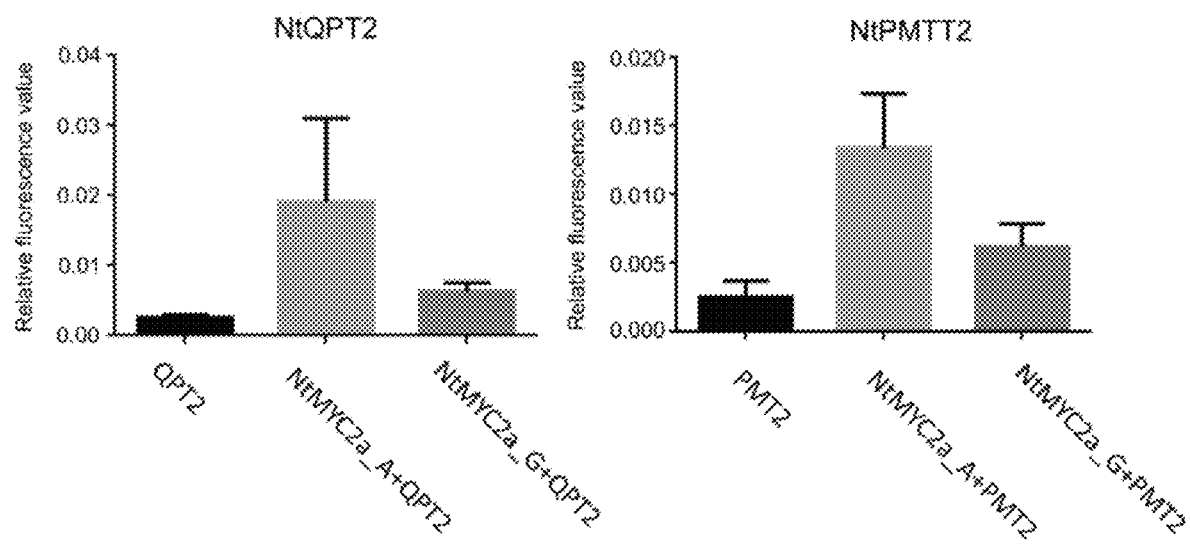
FIG. 2 is a histogram of fluorescence value of nicotine synthesis related enzyme gene promoter fragment expression when gene containing the SNP site of the molecular marker of the invention is overexpressed in experimental example 3 of the invention; the left picture shows fluorescence value of expression of promoter fragment of NtQPT2 gene related to nicotine synthesis, Wherein the sign QPT2 on abscissa refers to fluorescence value detected in tobacco transfected by *agrobacterium* transformed with NtQPT2 Pgreen0800 vector and pB2GW7 empty vector, the sign NtMYC2a_G+QTP2 refers to fluorescence value detected in tobacco transfected by *agrobacterium* transformed with NtMYC2a_A vector and NtQTP2 Pgreen0800 vector, and the sign NtMYC2a_G+QTP2 refers to fluorescence value detected in tobacco transfected by *agrobacterium* transformed with NtMYC2a_G vector and NtQTP2 Pgreen0800 vector; the right picture shows the fluorescence value of expression of promoter fragment of nicotine synthesis-related enzyme NtPMT2 gene, wherein the sign PMT2 on abscissa refers to fluorescence value detected in tobacco transfected by *agrobacterium* transformed with NtPMT2 Pgreen0800 vector and pB2GW7 empty vector, the sign NtMYC2a_A+PMT2 refers to fluorescence value detected in tobacco transfected *Agrobacterium* transformed with with NtMYC2a A vector and Nt PMT2 Pgreen0800 vector, and the sign NtMYC2a_G+PMT2 refers to fluorescence value detected in tobacco transfected by *agrobacterium* transformed with NtMYC2a_G vector and Nt PMT2 Pgreen0800 vector.

NtPMT2 Pgreen0800 vector + pB2GW7empty vector
NtQPT2 Pgreen0800 vector + pB2GW7 empty vector
NtMYC2a_A vector + NtPMT Pgreen0800 empty vector
NtMYC2a_G vector + NtPMT Pgreen0800 vector
NtMYC2a_A vector + NtQTP2 Pgreen0800 vector
NtMYC2a_G vector + NtQPT2 Pgreen0800 vector Leaves of 14 days old Ben's tobacco plants were injected by instantaneous transformation method, and then the injected Ben's tobacco was kept away from light for 24 hours, and restored to culture under light for 48 hours. Material taken from above Ben's tobacco was put into a 1.5 ml EP tube, with 2 steel balls with a diameter of 0.5 cm added, shaken and crushed at 60 Hz for 30 seconds at ultra-low temperature; 100 μL PLB lysate was added to the crushed powders, vibrated by vortex vibration for 10 seconds for rapidly dissolving so as to extract total protein; it's centrifugated at 4° C. 13000 rpm for 10 seconds and 8 μL of supernatant was absorbed and added to another EP tube, and 40 μL LAR II is added, mixed gently. it's detected for the first time by fluorescence spectrophotometer; After detection, 40 μL Stop&GloReagent was added, mixed gently and performed fluorescence detection again; it's found by recording and comparing detection value that NtMYC2a_A more significantly than NtMYC2a_G to activate tobacco NtPMT2 and NtQPT2 promoters (FIG. 2). It has been proven by report that NtPMT2 and NtQPT2 genes are two key enzymes in nicotine synthesis pathway, and activation on promoters of these two key enzyme genes is significantly positively correlated with nicotine synthesis and content. In other words, person skilled in the art can expect that nicotine content will increase with activation of promoters of these two key enzyme genes. Therefore, this experimental example further proves that overexpression of gene containing the SNP site of the invention can activate two key enzymes positively related to nicotine synthesis, and when the SNP site is A, the activation degree is significantly higher than that when the SNP site is G (FIG. 2).

Experimental Example 4: The Molecular Marker of the Invention Enhances the Interaction Effect with NtMED25

Figure 3:
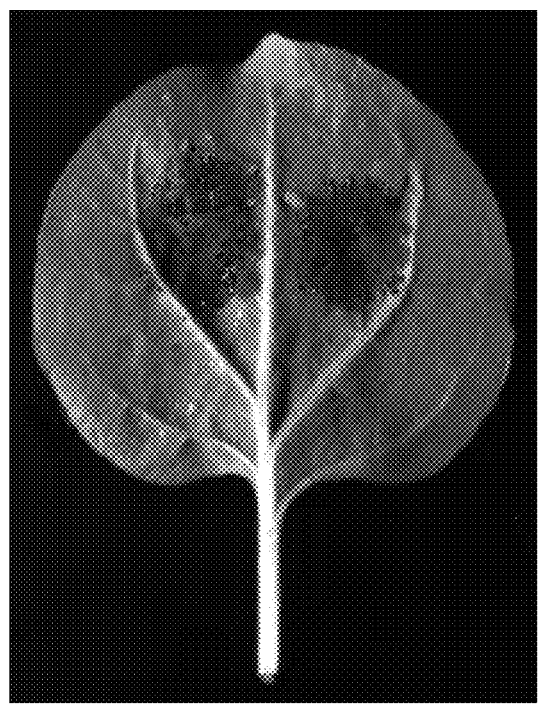
FIG. 3 is a fluorescent photograph of co-expressing gene fragment containing the SNP site of the molecular marker of this invention with gene NtMED25 in tobacco leaves of experimental example 4 of the invention. The left side of the leaf is fluorescence result of co-expressing AA genotype of the SNP site of the molecular marker of the present invention, the right side of the leaf is fluorescence result of co-expressing GG genotype of the SNP site of the molecular marker of the present invention.

NtMED25 can promote synthesis of nicotine. This experimental example verifies influence of different genotypes of SNP site of the invention on the binding strength of NtMED25, and proves that AA genotype of SNP site of the invention can bind and interact with NtMED25 gene more strongly than GG genotype, thus significantly influencing nicotine content. The full-length sequence of NtMED25 was cloned with primers NtMED25 F: AAGGTAC-Catgtgtaaaaatgcgttgggagctg (SEQ ID NO. 9) and NtMED25 R: AAGTCGACgggcatgtttggcagtcctcgtgaa (SEQ ID NO. 10), and then cloned into 1300 nLUC vector. Two NtMYC2 A/G fragments were cloned respectively with NtMYC2 F: TTGGTACCatgacggactatagaataccaacgatgacta (SEQ ID NO. 11) and NtMYC2 R: AAGTCGACtcgcgattcagcaattctggatgt-caatgat (SEQ ID NO. 12), and then connected respectively to pCAMBIA1300-cLUC vector to obtain NtMYC2 A/G 1300-cLUC expression vector and NtMED25 1300-nLUC expression vector. NtMYC2 A/G 1300-cLUC expression vector and NtMED25 1300-nLUC expression vector are co-transformed into Ben's tobacco leaves, and fluorescence intensity was observed 3 days later. Result is shown as FIG. 3. It's shown by the result that, AA genotype SNP fragment interact with NtMED25 strongerly with brighter fluorescence. On the contrary, GG genotype SNP fragment interact with NtMED25 weaker with darker fluorescence. The left picture of FIG. 3 shows AA genotype interation, and the right picture of FIG. 3 is GG genotype interation.

Experimental Example 5: Use of SNP Site in Breeding

In order to further identify use of the SNP site in breeding, in this example, the high nicotine tobacco variety of Honghua dajinyuan (nicotine content is 21.4 mg/g and genotype is AA) was hybridized with the low nicotine tobacco variety of Yunyan 87 (nicotine content is 9.4 mg/g and genotype is GG), and the harvested F1 seeds were planted. Genotype and nicotine content of F2 population and F1 individuals were detected. Genotype was detected by KASP (Kompetitive Allele Specific PCR) labeling the method and detection primers were MYC2a-F1 GTATCAAGAATCAAACAGATCTGAATTGAT-TTGTCT (SEQ ID NO. 1), MYC2a-R1 TGA-TAAAGTCAGGCGAAAACGA (SEQ ID NO. 2).

There were 54 strains with GG genotype in F2 population, and all of them had nicotine contents higher than 20 mg/g. The experimental results show that the accuracy of detecting genotype and phenotype of F2 population with the SNP site of the invention still reaches 100%.

What is claimed is:

1. A kit for identifying high or low nicotine content of tobacco, comprising a molecular marker Nicotine Associated SNP 1, wherein the molecular marker Nicotine Associated SNP 1 is a single nucleotide polymorphism SNP site Nitab4.5_0002539:95304 A/G at base No. 95304 of Genomic segment No. 0002539 in tobacco genome version of Nitab v4.5 Genome Scaffolds Edwards2017; the SNP site is located at the 324$^{th}$ nucleotide of the amplicon sequence set forth in SEQ ID NO: 13, which is derived from the tobacco genome using primers set forth in SEQ ID NO:1 and SEQ ID NO:2, and wherein the kit further comprises a pair of specific primers for the molecular marker Nicotine Associated SNP 1 comprising SEQ ID NO:1 and SEQ ID NO:2.

2. The kit for identifying high or low nicotine content of tobacco according to claim 1, further comprising: reagents for PCR, reagents for sequencing, and/or reagents for a genotyping assay.

3. A method for breeding tobacco varieties with high or low nicotine content, wherein tobaccos with high or low nicotine content from candidate tobaccos are screened by using a molecular marker Nicotine Associated SNP 1 for identifying high or low nicotine content of tobacco comprising a single nucleotide polymorphism (SNP) site Nitab4.5_0002539:95304 A/G at base No. 95304 of Genomic segment No. 0002539 in tobacco genome version of Nitab v4.5 Genome Scaffolds Edwards2017; the SNP site is located at the 324$^{th}$ nucleotide of the amplicon sequence set forth in SEQ ID NO:13, which is derived from the tobacco genome using primers set forth in SEQ ID NO:1 and SEQ ID NO:2.

4. The method for breeding tobacco varieties with high or low nicotine content according to claim 3, wherein tobacco with high nicotine content is selected as a female parent or a male parent, and tobacco required to be improved is selected as the male parent or the female parent, wherein a F1 generation is obtained by crossing the female parent and the male parent.

5. The method for breeding tobacco varieties with high or low nicotine content according to claim 4, wherein F2 generation plants are obtained by inbred F1 generation plants, and F2 generation plants are backcrossed with selected tobaccos with high or low nicotine content or tobaccos required to be improved.

6. The method for breeding tobacco varieties with high or low nicotine content according to claim 5, wherein tobaccos with high or low nicotine content are screened from the backcrossed population through a method for identifying high or low nicotine content of tobacco, and wherein a molecular marker Nicotine Associated SNP 1 is used to screen candidate tobaccos; the molecular marker Nicotine Associated SNP 1 is a SNP site Nitab4.5_0002539:95304 A/G at base No. 95304 of Genomic segment No. 0002539 in tobacco genome version of Nitab v4.5 Genome Scaffolds Edwards2017; the SNP site is located at the 324$^{th}$ nucleotide of the amplicon sequence set forth in SEQ ID NO: 13, which is derived from the tobacco genome using primers set forth in SEQ ID NO: 1 and SEQ ID NO:2.

\* \* \* \* \*